(12) United States Patent
Grab

(10) Patent No.: US 8,609,172 B2
(45) Date of Patent: Dec. 17, 2013

(54) ORGANIC COMPOUNDS AND METHODS

(75) Inventor: Willi Grab, Orpund (CH)

(73) Assignee: Givaudan SA, Vernier (CH)

( * ) Notice: Subject to any disclaimer, the term of this patent is extended or adjusted under 35 U.S.C. 154(b) by 738 days.

(21) Appl. No.: 12/375,351

(22) PCT Filed: Jul. 25, 2007

(86) PCT No.: PCT/CH2007/000367
§ 371 (c)(1),
(2), (4) Date: Jan. 27, 2009

(87) PCT Pub. No.: WO2008/011744
PCT Pub. Date: Jan. 31, 2008

(65) Prior Publication Data
US 2009/0263552 A1    Oct. 22, 2009

(30) Foreign Application Priority Data

Jul. 28, 2006  (SG) ................ 200605098-3
Aug. 11, 2006  (GB) .................... 0615898.4

(51) Int. Cl.
*A23L 1/226* (2006.01)
*C07C 69/675* (2006.01)
*C07D 313/04* (2006.01)

(52) U.S. Cl.
USPC ........... 426/536; 426/534; 549/271; 549/273; 560/180; 560/179

(58) Field of Classification Search
USPC ........................................................ 426/534
See application file for complete search history.

(56) References Cited

FOREIGN PATENT DOCUMENTS

| | | |
|---|---|---|
| EP | 0064326 A1 | 11/1982 |
| JP | 09031020 A | 2/1997 |
| JP | 10168029 A | 6/1998 |
| JP | 2001114732 A | 4/2001 |
| JP | 2002512629 A | 4/2002 |
| WO | 98/58899 A1 | 12/1998 |

OTHER PUBLICATIONS

XP002455207; Database WPI Week 200138, Derwent Publications Ltd., London, GB; AN 2001-364680.
English Language Abstract for JP2001114732.
English Language Abstract for JP0931020.
English Language Abstract for JP10168029.
Hisao Nemoto, et al., "Synthesis of Optically Active 8-Dodecalactone via Chiral Resolution Using CPF", Synlett 2007, No. 15, pp. 2343-2346, Aug. 23, 2007, New York.

*Primary Examiner* — Nikki H Dees
(74) *Attorney, Agent, or Firm* — Norris McLaughlin & Marcus PA

(57) ABSTRACT

A method of using organic compounds and providing slow release flavoring in or for food products wherein flavor precursors are added to flavor compositions and/or food products and release flavor compounds upon consumption of the food products, and novel flavor precursor compounds. The flavor precursors can be prepared from mono- and/or diglycerides and lactone flavor compounds.

23 Claims, No Drawings

ORGANIC COMPOUNDS AND METHODS

This is an application filed under 35 USC 371 of PCT/CH2007/000367.

The present invention relates to flavor precursors that can be added to food to slowly release the flavor upon heating and consumption.

Food products are rendered more palatable and more attractive for consumers by adding various flavors to them. However, when food products are processed or stored for a longer period of time, many flavors get lost at least partially, in particular the volatile flavors. For this reason, many attempts at encapsulation of flavors (binding to matrixes or coating to prevent premature release) have been made to retard the flavor release and prolong shelf life. These however are only partially successful, and there remains a need of a method or flavor product that keeps the main part of volatile flavors inside the food product to be slowly released upon consumption of the food by the consumer.

Applicant has now found that the use of flavor precursors according to formula I below in flavor compositions and food products provides a means to retard the premature release of volatile flavors and slowly release them upon consumption. Thereby an early unwanted flavor release, for example during storage or processing, is minimised, the shelf life of the flavored food product is prolonged and the flavor of the food product is improved.

SUMMARY OF THE INVENTION

In a first aspect, there is provided a method of providing a flavored food product, wherein at least one flavor precursor of formula I

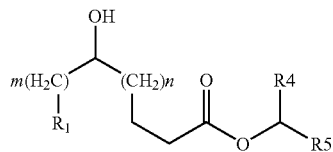

wherein R1 is selected from the group consisting of straight-chain C1 to C9 alkyl
wherein m and n are selected from 0 and 1, and if m is 0 then n is 1, and if m is 1 then n is 0.
wherein R4 is selected from H, $CH_2(OH)$, $CH_2(OCOR2)$,
wherein R5 is selected from $CH_2(OCOR3)$, $CH(OH)CH_2OCOR2$, $CH(OCOR3)CH_2OCOR2$, $CH(OCOR2)CH_2OH$,
wherein when R4 is selected from H, then R5 is selected from $CH(OH)CH_2OCOR2$, $CH(OCOR3)CH_2OCOR2$, and $CH(OCOR2)CH_2OH$,
wherein when R5 is $CH_2(OCOR3)$, then R4 is selected from $CH_2(OH)$, and $CH_2(OCOR2)$.
wherein R2 and R3 are independently selected from
a straight chain C1 to C17 alkyl, branched C3 to C17 alkyl, C6 to C17 alkenyl, C8 to 17 alkadienyl, a straight-chain C6 to C17 monoalkenyl, a branched C6 to C17 monoalkenyl,
a straight-chain C6 to C17 alkadienyl, a branched C6 to C17 alkadienyl,
a straight-chain C7 to C17 alkatrienyl, a branched C7 to C17 alkatrienyl,
a straight-chain C9 to C17 alkatetraenyl, a branched C9 to C17 alkatetraenyl,
a straight-chain C11 to C17 alkapentaenyl, a branched C11 to C17 alkapentaenyl, is admixed to a food product in a sufficient concentration to release a flavor of noticeable aroma upon consumption and/or heating of the food product.

In another aspect, there is provided a flavor composition comprising at least one flavor precursor as herein defined and food additives.

In another aspect, there is provided a food product comprising at least one flavor precursor as herein defined.

In another aspect, there is provided a flavor precursor of formula I as herein defined.

In another aspect, there is provided a process of forming the flavor precursor as herein defined by reacting at least one lactone flavor compound with at least one mono- and/or diglyceride in an acid catalised reaction.

DETAILED DESCRIPTION OF THE INVENTION

In one embodiment, there is provided a flavor composition comprising a mixture of flavor precursors as herein defined, formed by reacting at least one flavor compound comprising a lactone group with at least one mono- or diglyceride in an acid catalised reaction, and food additives.

In another embodiment, there is provided a food product comprising a mixture of flavor precursors as herein defined formed by reacting at least one lactone flavor compound with at least one mono- or diglyceride in an acid catalised reaction.

In another embodiment, there is provided a flavor precursor as herein defined wherein
R1 is selected from the group consisting of straight-chain C1 to C9 alkyl and a straight-chain C2 to C9 alkenyl and
wherein R2 and R3 are independently selected from
a straight chain C1 to C17 alkyl, branched C3 to C17 alkyl, C6 to C17 alkenyl, C8 to 17 alkadienyl
a straight-chain C6 to C17 monoalkenyl, a branched C6 to C17 monoalkenyl,
a straight-chain C6 to C17 alkadienyl, a branched C6 to C17 alkadienyl,
a straight-chain C7 to C17 alkatrienyl, a branched C7 to C17 alkatrienyl,
a straight-chain C9 to C17 alkatetraenyl, a branched C9 to C17 alkatetraenyl,
a straight-chain C11 to C17 alkapentaenyl, and a branched C11 to C17 alkapentaenyl.

In another embodiment, there is provided a flavor precursor as defined herein above wherein R1 is a straight-chain C1 to C9 alkyl selected from the group consisting of methyl, ethyl, propyl, butyl, pentyl, hexyl, heptyl, octyl, and nonyl.

In another embodiment, there is provided a flavor precursor as defined herein above wherein R2 and R3 are independently selected from the group consisting of C1, C2, C3, C4, C5, C6, C7, C8, C9, C10, C11, C13, C15, and C17 alkyl.

In another embodiment, there is provided a flavor precursor as defined herein above wherein R2 and R3 are independently selected from the group consisting of C6, C7, C8, C9, C10, C11, C13, C15, and C17 alkenyl, a C17-8en (oleic acid residue) alkenyl, a C17-8,11 alka-dienyl (linoleic acid residue), and a C17-8,11,14-trienyl (linolenic acid residue).

In another embodiment, there is provided a flavor precursor as defined herein above wherein R2 and R3 are straight-chain residues.

In another embodiment, there is provided a flavor precursor as defined herein above wherein R2 and R3 are selected from C4 to C17 residues.

In another embodiment, there is provided a flavor precursor as defined herein above wherein R2 and R3 are selected from the group consisting of
a straight chain C1 to C17 alkyl, branched C3 to C17 alkyl, C6 to C17 alkenyl, C8 to 17 alkadienyl
a straight-chain C6 to C17 monoalkenyl, a branched C6 to C17 monoalkenyl, a straight-chain C6 to C17 alkadienyl, a branched C6 to C17 alkadienyl,
a straight-chain C7 to C17 alkatrienyl, and a branched C7 to C17 alkatrienyl.

In another embodiment, there is provided a flavor precursor as defined herein above wherein n is 0 and m is 1.

In another embodiment, there is provided a flavor precursor as defined herein above wherein n is 1 and m is 0.

In another embodiment, there is provided a flavor precursor as defined herein above wherein the lactone flavor residue R1-(CH$_2$)$_m$—COH—(CH$_2$)$_n$—CH$_2$—CH$_2$—CO is selected from the group consisting of a residue of gamma hexylactone, gamma heptalactone, gamma octalactone, gamma nonalactone, gamma decalactone, gamma decenolactone, gamma undecalactone, gamma dodecalactone, gamma tridecalactone, and gamma tetradecalactone.

In another embodiment, there is provided a flavor precursor as defined herein above wherein the lactone flavor residue R1-(CH$_2$)$_m$—COH—(CH$_2$)$_n$—CH$_2$—CH$_2$—OC is selected from the group consisting of a residue of delta hexylactone, delta heptalactone, delta octalactone, delta nonalactone, delta decalactone, delta decenolactone, delta undecalactone, delta dodecalactone, delta tridecalactone, and delta tetradecalactone.

In another embodiment, there is provided a flavor precursor as defined herein above wherein the flavor precursor will release a gamma lactone and the flavor precursor is selected from the group consisting of a flavor precursor wherein m=1, n=0, R4=H, R5=CH(OH)CH$_2$OCOR2, flavor precursor wherein m=1, n=0, R4↑H, R5=CH(OCOR3)CH$_2$OCOR2, flavor precursor wherein m=1, n=0, R4=CH$_2$(OCOR2), R5=CH$_2$(OCOR3), flavor precursor wherein m=1, n=0, R4=CH$_2$(OH), R5=CH$_2$(OCOR3), and flavor precursor wherein m=1, n=0, R4=H, R5=CH(OCOR3)CH$_2$OH.

In another embodiment, there is provided a method as defined herein-above wherein the flavor precursor will release a delta lactone and the flavor precursor is selected from the group consisting of a flavor precursor wherein m=0, n=1, R4=H, R5=CH(OCOR3)CH$_2$OCOR2, flavor precursor wherein m=0, n=1, R4=CH$_2$(OCOR2), R5=CH$_2$(OCOR3), flavor precursor wherein m=0, n=1, R4=CH$_2$(OH), R5=CH$_2$(OCOR3), and flavor precursor wherein m=0, n=1, R4=H, R5=CH(OCOR3)CH$_2$OH.

In another embodiment, there is provided a process of forming the flavor precursor as herein defined by reacting a mixture of glycerides selected from mono- and/or diglycerides derived from a suitable natural sources which is prepared by stirring a sufficient amount of fat or oil from a natural source with a sufficient amount of glycerine, catalyzed by a sufficient amount of catalyst in a reaction container at a suitable temperature for a sufficient time with at least one lactone flavor compound.

In another embodiment, there is provided a process as herein defined wherein the natural source is selected from an animal source including butter fat, chicken fat, beef tallow, and fish oil.

In another embodiment, there is provided a process as herein defined wherein the natural source is selected from a botanical source including cocoa butter, hazelnut oil, peanut oil, and coconut fat.

The flavor precursors of formula I are hydroxyesters of gamma or delta lactones with mono- or diglycerides that form hydroxy-diglyceride ester or hydroxy-triglyceride ester precursors. They slowly release volatile flavors (aroma) and thereby protect the chemically bound flavor from an undesired excessive release of the volatile flavor compound, for example during processing and storage of a food product. The flavor is slowly released in presence of water and enzymes that are present naturally in the mouth during consumption.

Lactone flavor precursors ((1- and 2-(4 or 5-hydroxy)-glyceridesters) that can release lactones) for use in the present invention can be formed as follows. Lactone flavor compounds react with mono- or diglycerides (1-acylglycerides, 2-acylglycerides, 1,2-diacylglycerides and 1,3-diacylglycerides) in an acid-catalised reaction as shown in the reaction scheme below.

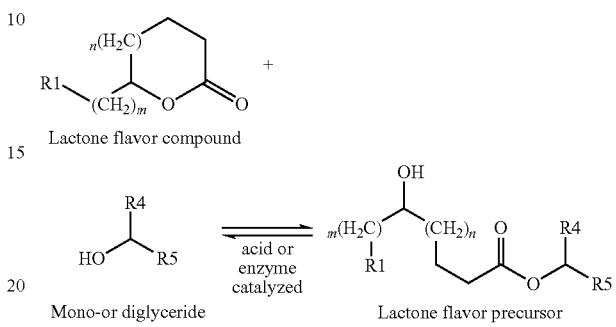

FIG. 1 Formation of lactone flavor precursors of Fl and release of lactone flavor compounds in the reversible reaction of lactone flavors with mono- and/or di-glycerides Formation (and release) of the flavor precursors occurs in the presence of H$^+$, as shown in FIG. 1 (for the formation: left to right direction of the reaction scheme).

The flavor precursors have no aroma. These flavor precursors will then slowly release the lactone flavor in a reversed reaction when exposed to aqueous acidic conditions as shown in FIG. 1 (right to left direction of the reaction scheme), for example upon heating in the presence of water (for example by cooking or by baking) and in particular upon consumption since the mouth contains enzymes that increase the speed of the flavor release.

The flavors that form a precursor when reacted with mono- and/or diglycerides and are later released by the formed precursors in methods according to the invention consist of gamma and delta lactones.

For example, without limitation, a precursor of formula I wherein R1=propyl and m=1 and n=0 will release gamma octalactone, a precursor of formula I wherein R1=butyl and m=0 and n=1 will release delta nonalactone.

Some examples of groups of precursor compounds are shown below.

The following flavor precursors are gamma lactones glyceride ester compounds and will release gamma lactones:

| No. | structural formula of gamma lactone glyceride ester flavor precursor compounds |
|---|---|
| 1 | 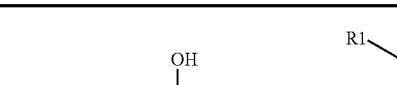 m = 1, n = 0, R4 = H, R5 = CH(OH)CH$_2$OCOR2 |

| No. | structural formula of gamma lactone glyceride ester flavor precursor compounds |
|---|---|
| 2 | 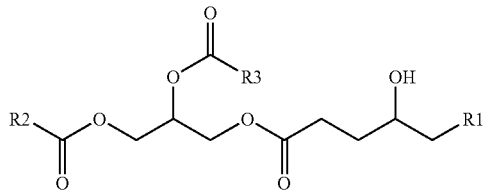<br>m = 1, n = 0, R4 = H, R5 = CH(OCOR3)CH₂OCOR2 |
| 3 | 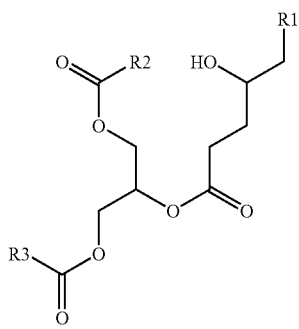<br>m = 1, n = 0, R4 = CH₂(OCOR2), R5 = CH₂(OCOR3) |
| 4 | 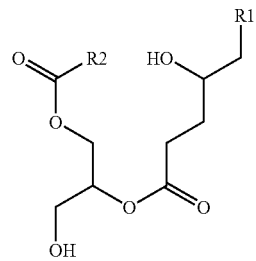<br>m = 1, n = 0, R4 = CH₂(OH), R5 = CH₂(OCOR3) |
| 5 | 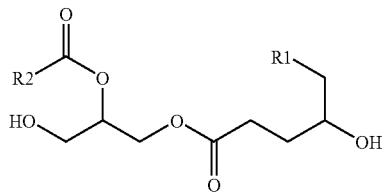<br>m = 1, n = 0, R4 = H, R5 = CH(OCOR2)CH₂OH |

The following delta lactone glyceridester flavor precursor compounds will release delta lactones:

| No. | structural formula of delta lactone glyceride ester flavor precursor compounds |
|---|---|
| 1 | 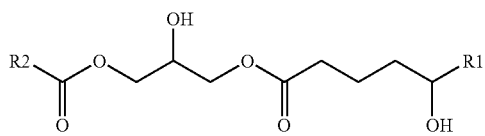<br>m = 0, n = 1, R4 = H, R5 = CH(OH)CH₂OCOR2 |
| 2 | 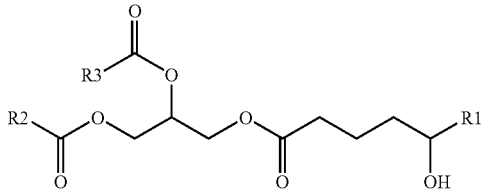<br>m = 0, n = 1, R4 = H, R5 = CH(OCOR3)CH₂OCOR2 |
| 3 | 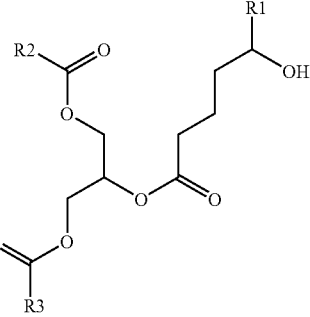<br>m = 0, n = 1, R4 = CH₂(OCOR2), R5 = CH₂(OCOR3) |
| 4 | 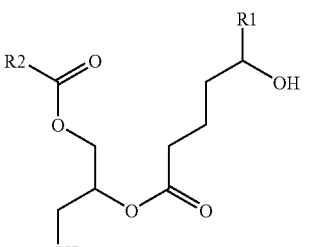<br>m = 0, n = 1, R4 = CH₂(OH), R5 = CH₂(OCOR3) |
| 5 | 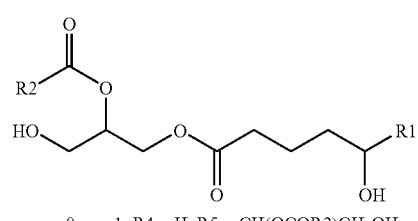<br>m = 0, n = 1, R4 = H, R5 = CH(OCOR2)CH₂OH |

Mono- and diglycerides used to prepare the flavor precursors of the invention can be synthesized by know chemical processes as described, for example, in JP2001181271. Alternatively they can be prepared from natural sources including botanical and animal sources by enzymatic or chemical hydrolysis, as is well-known in the art. Some mono- and diglycerides are available commercially as a mixture or in pure form (either extracted or synthesized). For example, without limitation, botanical sources of mono- and di-glycerides include palm oil, oil seeds, sunflower seeds, nuts, cacao beans, coconuts, hazelnuts, peanuts, and many more. For example, without limitation, animal sources of mono- and di-glycerides include milk, butter, meat, chicken, beef, pork, lamb, fish, and many more.

For example, a mixture of mono- and/or diglycerides derived from natural sources (for example butter fat) can be prepared by stirring a sufficient amount of naturally derived fat with a sufficient amount of glycerine, catalyzed by a sufficient amount of catalyst (for example acid, enzyme, Lipase) in a reaction container at a suitable temperature for a sufficient time. Such processes are well known and will be apparent to the skilled person.

A typical mixture of mono- and diglycerides derived from natural sources includes mono- and di-glycerides bound to saturated fatty acids including laurylmonoglyceride (C12—forms Fl with R1=C11), myristylmonoglyceride (C14—forms Fl with R1=C13), palmitylmonoglyceride (C16—forms Fl with R1=C15), and stearoylmonoglyceride (C18—forms Fl with R1=C17). Monoglycerides comprising unsaturated fatty acids include oleylmonoglyceride, linolylmonoglyceride, and alpha-linolenylmonoglyeride.

A typical mixture of monoglycerides derived from cocoa butter includes palmitylmonoglyceride (C16), oleylmonoglyceride (C18-1, with one double bond), and stearoylmonoglyceride (C18).

A typical mixture of monoglycerides derived from miglyol, a commonly used oil from vegetable sources), includes C8, C10, and C12 monoglycerides.

A typical mixture of monoglycerides derived from butter includes mainly C4, C6, C8, C10, C12, C14, C16, C18 saturated monoglycerides.

Mono- and diglycerides can also be formed from short chain fatty acids like acetate, propionate or butyrate (acetin, diacetin, monopropionin, dipropionin, monobutyrin, dibutyrin: glycerin dibutyrate).

When used in food, mono- and diglycerides and part of their residues (R2, R3) can partially degrade over time and release free fatty acids (R2-COOH for monoglyceride derived precursor residues, R2-COOH and R3-COOH for diglyceride derived precursor residues), which may turn a product rancid. When choosing a particular precursor for a particular food product, R2 and R3 of the flavor precursor of formula 1 will be chosen so that upon potential R2/R3 degradation an acid compound without undesired off-note, for example caprylic acid, will be released. Such an acid compound contributes to the desired flavor note rather than, for example, lauric acid, which will result in an undesirable soapy off-note in the chosen food product. Whether a particular flavor note is considered an off-note will depend on the food product the flavor is added to, and the desired flavor note, as will be apparent to the skilled person, and the specific choice of appropriate R2 and R3 is well within the experience of the skilled person.

Commercial mono- and diglycerides are mixtures of mainly 1-acylglycerides or 1,3-diacylglycerides with variable amounts of 2-acylglycerides and other glycerides.

1-acylglycerides when reacted with lactone flavor compounds as described herein will form flavor precursors of formula I wherein R4 is H and R5 is $CH(OH)CH_2OCOR2$ and flavor precursors of formula I wherein R4 is $CH_2(OH)$ and R5 is $CH_2OCOR2$.

2-Acylglycerides when reacted with lactone flavor compounds as described herein will form flavor precursors of formula I wherein R4 is H and R5 is $CH(OCOR2)CH_2OH$ 1,3-diglycerides when reacted with lactone flavor compounds as described herein will form flavor precursors of formula I wherein R4 is $CH_2(OCOR2)$ and R5 is $CH_2(OCOR3)$.

Flavors are compounds that can be detected by the human olfactory system. To provide sensory properties, a flavor must have the following molecular properties: some water solubility, a sufficiently high vapor pressure, low polarity, and some ability to dissolve in fat (lipophilicity). Flavor compounds have a molecular weight of up to 294 (no larger compounds are known to trigger the human olfactory system).

Lactone flavors useful for the methods described herein are gamma or delta lactone compounds that can be reacted with the mono- and diglycerides as described herein. These flavors include but are not limited to gamma hexylactone, gamma heptalactone, gamma octalactone, gamma nonalactone, gamma decalactone, gamma decenolactone, gamma undecalactone, gamma dodecalactone, gamma tridecalactone, gamma tetradecalactone, delta hexylactone, delta heptalactone, delta octalactone, delta nonalactone, delta decalactone, delta decenolactone, delta undecalactone, delta dodecalactone, delta tridecalactone, and delta tetradecalactone.

Useful lactone flavors include natural and artificial flavors, and extracts from natural sources that contain a mixture of flavor compounds including lactones flavors, and lactone flavor compounds as such. A number of suitable flavors can be found, for example, in the BACIS database (Boelens Aroma Chemical Information Service), which includes the FlavorBase 2004 database (Leffingwell & Associates, Canton, Ga., USA), in the listing of Flavor chemicals on the FDA (Food & Drug Administration, USA) & FEMA GRAS lists (FEMA—Flavor and Extracts Manufacturers Association, GRAS—Generally Recognised As Safe), and the European Community (EC) Register list.

The lactone flavor precursor can be added directly to a food product, or can be provided as a flavor composition comprising further food additives to be added to food products.

The term "food product" as used herein includes any food product, for example, without limitation, cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, cheese products, butter and butter substitute products, milk substitute products, soy products, edible oils and fat products, medicaments, beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages.

A flavor composition according to the invention is a composition that comprises a lactone flavor precursor, a food additive, and optionally additional flavors. Food additives are well known and may be selected from, for example, without limitation, solvents, binders, diluents, disintegrating agents, lubricants, coloring agents, preservatives, antioxidants, emulsifiers, stabilisers, flavor-enhancers, sweetening agents, anti-caking agents, and the like.

Examples of such carriers or diluents for flavor or fragrance compounds may be found e.g. in "Perfume and Flavor Materials of Natural Origin", S. Arctander, Ed., Elizabeth, N.J., 1960; in "Perfume and Flavor Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

The flavor composition may be added in any suitable form, for example as a liquid, as a paste, or in encapsulated form bound to or coated onto carriers/particles or as a powder.

There now follows a series of non-limiting examples that serve to illustrate the invention.

EXAMPLES

Unless stated otherwise, all % indicated are in wt/wt.

Example 1

Preparation of Precursor Compounds from Glycerin-monodecanoate and Release of Flavor Compounds by Heat Hydrolysis or Enzyme/Acid Catalysis in the Mouth The precursor is prepared as follows: 1 g of Glycerin-monodecanoate (also known as CAS 2277-23-8 or 1-Mono-caprin, commercially available from Indofine) and 500 mg (unless otherwise stated) of a lactone flavor compound are dissolved in 20 ml hexane with a trace of HCl conc. as catalyst in a round bottom flask and boiled under reflux for about 3 hours. To the mixture, 0.5 ml of a saturated brine solution is added, and the mixture is shaken. The organic phase (hexane) is separated and dried with a small amount of Magnesium sulfate. The hexane is distilled off under vacuum. The resulting precursor material is further purified by chromatography.

All tested lactone precursors are almost odourless even at a concentration near 100%.

When the precursor is boiled in water at 0.1%, the aroma of the reacted lactone is released (compare examples 2-4).

The precursor (10 ppm) is tasted in an aqueous 5% sugar solution at room temperature, and a weak, bland, slowly developing aroma of the corresponding lactone is detected (compare examples 2-4).

Example 2

5,11-Dihydroxi-8,14-dioxo-9,13-dioxa-heneicosan (1-octanoyl-3-(4-hydroxi)-octanoyl-glyceride) flavor precursor

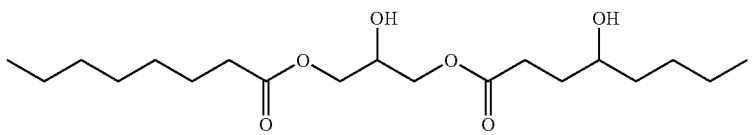 [SMILES: CCCCCCCC(=O)OCC(O)COC(=O)CCC(O)CCCC]

The precursor is a compound of formula I with n=0, m=1, R1=propyl, R2=$C_7H_{15}$, R4=H, R5 is $CH(OH)CH_2OCOR2$, R2=heptyl, and is able to release gamma octalactone.

The precursor is prepared using Glycerin-monodecanoate and gamma octalactone as described in example 1. The purified precursor is a waxy odorless paste.

When the precursor is boiled in water, a creamy coconut-like aroma (the aroma of gamma octalactone) is released.

Upon tasting of the precursor (10 ppm) in an aqueous 5% sugar solution at room temperature, a bland slowly developing taste of a mellow, creamy coconut aroma with a soft mouthfeel is detected.

Example 3

6,13-Dihydroxi-10,16-dioxo-11,15-dioxa-pentacosan (1-decanoyl-3-(5-hydroxi)-decanoyl-glyceride) flavor precursor

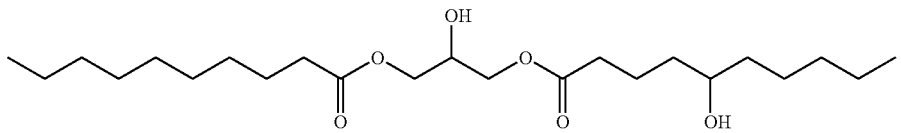 [SMILES: CCCCCCCCCC(=O)OCC(O)COC(=O)CCCC(O)CCCCC]

The precursor is a compound of formula I with n=1, m=0, R1=pentyl, R2=nonyl, R4=H, R5=$CH(OH)CH_2OCOR2$ and is able to release delta decalactone.

The precursor is prepared using Glycerin-monodecanoate and delta decalactone as described in example 1. The purified precursor is a waxy paste without odor.

When the precursor is boiled in water, a buttery, creamy, aroma (the aroma of delta decalactone) is released.

Upon tasting of the precursor (10 ppm) in an aqueous 5% sugar solution at room temperature, a bland slowly developing taste of a creamy, buttery aroma with a soft mouthfeel is detected.

Example 4

13,20-Dihydroxi-10,16-dioxo-11,15-dioxa-dotria-cont-1-en (1-dec-9-enoyl-3-(5-hydroxi)-dodecanoyl-glyceride) flavor precursor

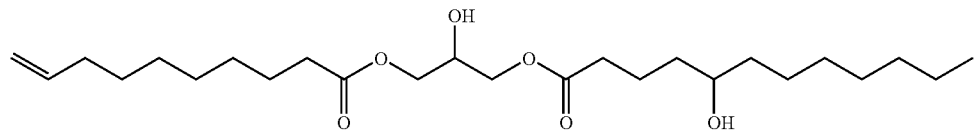 [SMILES: C=CCCCCCCCC(=O)OCC(O)COC(=O)CCCC(O)CCCCCCC]

The precursor compound is a compound of formula I with n=1, m=0, R1=heptyl, R2=8-nonenyl, R4=H, R5=CH(OH)(CH$_2$OCOR2) that is able to release delta dodecalactone.

The precursor is prepared using 1-Glycerindec-9-enoate and delta dodecalactone as described in example 1 subject to the following modification: 1 g of Glycerin-monodecanoate is replaced with 1 g 1-Glycerindec-9-enoate, which is synthesized as described below and reacted with 500 mg of delta dodecalactone as described in example 1. The purified precursor is a waxy paste without odor.

When the precursor is boiled in water, a mild, buttery, creamy, aroma (the aroma of delta dodecalactone) is released.

Upon tasting of the precursor (10 ppm) in an aqueous 5% sugar solution at room temperature, a bland slowly developing taste of a mild, buttery, creamy, aroma with a soft mouthfeel is detected.

Synthesis of 1-Glycerindec-9-enoate:

10 g of 9-Decenoic acid (CAS 14436-32-9, Bedoukian), 10 g of glycidol (CAS 556-52-5, Aldrich) and 100 mg Amberlyst A-26(OH) (Aldrich) are boiled under reflux with 200 ml hexane in a round bottom flask with reflux condenser and magnetic stirrer for 24 hours. The solution is filtered and the volatiles are distilled off under vacuum. The formed 1-Glycerindec-9-enoate purified further by chromatography.

Example 5

Butter Flavor Precursor

Preparation of Butter-Monoglyceride:

A mixture of monoglycerides, derived from butter fat is prepared by stirring 60 g butter fat with 20 g glycerine, catalyzed by 600 mg of Lipozyme RM IM (Novozyms) in a round bottom flask at 50° C. for 24 hours.

For the topnote, 2.0 g each of delta nonalactone, delta decalactone, delta undecalactone and delta dodecalactone are mixed.

For the top aroma, 1 g topnote are mixed with 99 g miglyol (vegetable oil). The top aroma has a strong lactone-butter aroma.

Preparation of the Precursors:

1 g of top note is mixed with 20 g of Butter-Monoglyceride and heated for 10 hours in a round bottom flask with reflux cooler to form the precursors. The resulting cooled precursor mixture has a weak lactony-butter aroma.

Comparison of Precursors and Top Aroma in Biscuits:

A biscuit short dough is prepared as follows:

| Ingredients: | % (wt/wt) |
|---|---|
| 1) Plain Flour (~10% (wt/wt) protein level) | 52.31 |
| 2) Vegetable Shortening BM 3030 (Woodlands Sunny Foods, Senoko, Singapore) | 17.26 |

-continued

| Ingredients: | % (wt/wt) |
|---|---|
| 3) Fine Milled Sugar | 17.40 |
| 4) Glucose Syrup 42 DE | 3.45 |
| 5) Skim Milk Powder | 1.49 |
| 6) Salt | 0.25 |
| 7) Sodium Bicarbonate | 0.31 |
| 8) Ammonium Bicarbonate | 0.21 |
| 10a) top aroma | 0.2 |
| 10b) precursors | 0.1 |
| | add 100.00 (water) |

Ingredients 2-6 are pre-blended in the mixing bowl, and mixed at low speed, then mixed further at medium speed for about 3 minutes. At low speed, the pre-dissolved solutions of sodium bicarbonate, ammonium carbonate, and 0.2% (wt/wt) of the top aroma or 0.1% (wt/wt) of the precursors are added; then the remaining water is added and mixed for 1 minute. Mixing is continued at medium speed for about 3 minutes to form a homogenous mixture. The flour is added at low speed to obtain a dough. The dough is formed to a sheet of a thickness of 4 mm and cut into biscuit shapes using a stamp cutter. Biscuits are baked on a wire tray at a temperature of 200° C. for about 8 to 10 minutes.

0.2% of the top aroma or 0.1% of the precursors are homogenously mixed with the dough. Biscuits are formed and baked at an oven temperature of 200° C. for 20 min.

During the baking process a strong butter aroma from the baking oven is observed for the top aroma biscuits, but which is very weak for the precursor biscuits. The sensory evaluation shows a stronger aroma in the top aroma biscuits.

After 2 months storage at room temperature a sensory evaluation is performed. The top aroma sample is bland, has lost its original butter aroma, and has a dry texture and mouth feel.

The precursor biscuits show a nice, balanced mild butter aroma and smooth, lasting buttery mouth feel.

The invention claimed is:
1. A method of providing a flavored food product, wherein at least one flavor precursor of formula I

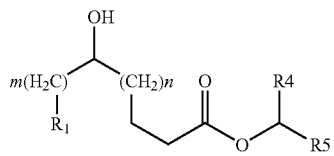

wherein R1 is selected from the group consisting of straight-chain C1 to C9 alkyl,
wherein m and n are selected from 0 and 1, and if m is 0 then n is 1, and if m is 1 then n is 0,
wherein R2 and R3 are independently selected from
a straight chain C1 to C17 alkyl, branched C3 to C17 alkyl, C6 to C17 alkenyl, C8 to 17 alkadienyl, a straight-chain C6 to C17 monoalkenyl, a branched C6 to C17 monoalkenyl,
a straight-chain C6 to C17 alkadienyl, a branched C6 to C17 alkadienyl,
a straight-chain C7 to C17 alkatrienyl, a branched C7 to C17 alkatrienyl,
a straight-chain C9 to C17 alkatetraenyl, a branched C9 to C17 alkatetraenyl,
a straight-chain C11 to C17 alkapentaenyl, a branched C11 to C17 alkapentaenyl,
wherein R4 is selected from H, $CH_2(OH)$, $CH_2(OCOR2)$,
wherein R5 is selected from $CH_2(OCOR3)$, $CH(OH)CH_2OCOR2$, $CH(OCOR3)CH_2OCOR2$, $CH(OCOR2)CH_2OH$,
wherein when R4 is selected from H, then R5 is selected from $CH(OH)CH_2OCOR2$, $CH(OCOR3)CH_2OCOR2$, and $CH(OCOR2)CH_2OH$,
wherein when R5 is $CH_2(OCOR3)$, then R4 is selected from $CH_2(OH)$, and $CH_2(OCOR2)$,
is admixed to a food product in a sufficient concentration to release a flavor of noticeable aroma upon consumption or heating of the food product.

2. A flavor precursor of formula I

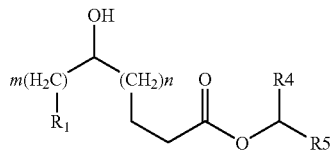

wherein R1 is selected from the group consisting of straight-chain C1 to C9 alkyl,
wherein m and n are selected from 0 and 1, and if m is 0 then n is 1, and if m is 1 then n is 0,
wherein R2 and R3 are independently selected from
a straight chain C1 to C17 alkyl, branched C3 to C17 alkyl, C6 to C17 alkenyl, C8 to 17 alkadienyl, a straight-chain C6 to C17 monoalkenyl, a branched C6 to C17 monoalkenyl,
a straight-chain C6 to C17 alkadienyl, a branched C6 to C17 alkadienyl,
a straight-chain C7 to C17 alkatrienyl, a branched C7 to C17 alkatrienyl,
a straight-chain C9 to C17 alkatetraenyl, a branched C9 to C17 alkatetraenyl,
a straight-chain C11 to C17 alkapentaenyl, a branched C11 to C17 alkapentaenyl,
wherein R4 is selected from H, $CH_2(OH)$, $CH_2(OCOR2)$,
wherein R5 is selected from $CH_2(OCOR3)$, $CH(OH)CH_2OCOR2$, $CH(OCOR3)CH_2OCOR2$, $CH(OCOR2)CH_2OH$,
wherein when R4 is selected from H, then R5 is selected from $CH(OH)CH_2OCOR2$, $CH(OCOR3)CH_2OCOR2$, and $CH(OCOR2)CH_2OH$,
wherein when R5 is $CH_2(OCOR3)$, then R4 is selected from $CH_2(OH)$, and $CH_2(OCOR2)$.

3. A flavor composition comprising a mixture of flavor precursors as defined in claim 2, which flavor precursors are formed by reacting at least one flavor compound comprising a lactone group with at least one mono- or diglyceride in an acid catalised reaction, and food additives.

4. A food product comprising at least one flavor precursor as defined in claim 2.

5. A food product comprising a mixture of flavor precursors as defined in claim 2, which flavor precursors are formed by reacting at least one lactone flavor compound with at least one mono- or diglyceride in an acid catalised reaction.

6. A flavor composition comprising at least one flavor precursor as defined in claim 2 and food additives.

7. A flavor precursor of formula (I) according to claim 2 wherein R1 is selected from the group consisting of straight-chain C1 to C9 alkyl and a straight-chain C2 to C9 alkenyl and wherein R2 and R3 are independently selected from a straight chain C1 to C17 alkyl, branched C3 to C17 alkyl, C6 to C17 alkenyl, C8 to 17 alkadienyl, a straight-chain C6 to C17 monoalkenyl, a branched C6 to C17 monoalkenyl, a straight-chain C6 to C 17 alkadienyl, a branched C6 to C 17 alkadienyl,
a straight-chain C7 to C 17 alkatrienyl, a branched C7 to C 17 alkatrienyl,
a straight-chain C9 to C17 alkatetraenyl, a branched C9 to C17 alkatetraenyl,
a straight-chain C11 to C17 alkapentaenyl, and a branched C11 to C17 alkapentaenyl.

8. A flavor precursor according to claim 7 wherein R1 is a straight-chain C1 to C9 alkyl selected from the group consisting of methyl, ethyl, propyl, butyl, pentyl, hexyl, heptyl, octyl, and nonyl.

9. A flavor precursor according to claim 7 wherein R2 and R3 are independently selected from the group consisting of C1, C2, C3, C4, C5, C6, C7, C8, C9, C10, C11, C13, C15, and C17 alkyl.

10. A flavor precursor according to claim 7 wherein R2 and R3 are independently selected from the group consisting of C6, C7, C8, C9, C10, C11, C13, C15, and C17 alkenyl, a C17-8en (oleic acid residue) alkenyl, a C17-8,11 alka-dienyl (linoleic acid residue), and a C17-8,11,14-trienyl (linolenic acid residue).

11. A flavor precursor according to claim 7 wherein R2 and R3 are straight-chain residues.

12. A flavor precursor according to claim 7 wherein R2 and R3 are selected from C4 to C17 residues.

13. A flavor precursor according to claim 7 wherein R2 and R3 are selected from the group consisting of
a straight chain C1 to C17 alkyl, branched C3 to C17 alkyl, C6 to C17 alkenyl, C8 to 17 alkadienyl, a straight-chain C6 to C 17 monoalkenyl, a branched C6 to C 17 monoalkenyl, a straight-chain C6 to C17 alkadienyl, a branched C6 to C17 alkadienyl, a straight-chain C7 to C17 alkatrienyl, and a branched C7 to C17 alkatrienyl.

14. A flavor precursor of formula I according to claim 2 wherein n is 0 and m is 1.

15. A flavor precursor of formula I according to claim 2 wherein n is 1 and m is 0.

16. A flavor precursor according to claim 14 wherein the lactone flavor residue R1-$(CH_2)_m$—COH—$(CH_2)_n$—$CH_2$—$CH_2$—CO is selected from the group consisting of a residue of gamma hexalactone, gamma heptalactone, gamma octalactone, gamma nonalactone, gamma decalactone, gamma decenolactone, gamma undecalactone, gamma dodecalactone, gamma tridecalactone, and gamma tetradecalactone.

17. A flavor precursor according to claim 15 wherein the lactone flavor residue R1-$(CH_2)_m$—COH—$(CH_2)_n$—$CH_2$—$CH_2$—OC is selected from the group consisting of a residue of delta hexylactone, delta heptalactone, delta octalactone, delta nonalactone, delta decalactone, delta decenolactone, delta undecalactone, delta dodecalactone, delta tridecalactone, and delta tetradecalactone.

18. A flavor precursor of formula I according to claim 2 wherein the flavour precursor will release a gamma lactone and the flavor precursor is selected from the group consisting of a flavor precursor wherein m=1, n=0, R4=H, R5=CH(OH)CH$_2$OCOR2, flavor precursor wherein m=1, n=0, R4=H, R5=CH(OCOR3)CH$_2$OCOR2, flavor precursor wherein m=1, n=0, R4=CH$_2$(OCOR2), R5=CH$_2$(OCOR3), flavor precursor wherein m=1, n=0, R4=CH$_2$(OH), R5=CH$_2$(OCOR3), and flavor precursor wherein m=1, n=0, R4=H, R5=CH(OCOR3)CH$_2$OH.

19. A flavour precursor of formula I according to claim 2 wherein the flavor precursor will release a delta lactone and the flavor precursor is selected from the group consisting of a flavor precursor wherein m=0, n=1, R4=H, R5=CH(OCOR3)CH$_2$OCOR2, flavor precursor wherein m=0, n=1, R4=CH$_2$(OCOR2), R5=CH$_2$(OCOR3), flavor precursor wherein m=0, n=1, R4=CH$_2$(OH), R5=CH$_2$(OCOR3), and flavor precursor wherein m=0, n=1, R4=H, R5=CH(OCOR3)CH$_2$OH.

20. A process of forming a flavor precursor of formula I according to claim 2 by reacting at least one lactone flavor compound with at least one mono- and/or diglyceride in an acid catalised reaction.

21. A process of forming a flavor precursor of formula I according to claim 2 by reacting a mixture of glycerides selected from mono-and/or diglycerides derived from a suitable natural sources which is prepared by stirring a sufficient amount of fat or oil from a natural source with a sufficient amount of glycerine, catalyzed by a sufficient amount of catalyst in a reaction container at a suitable temperature for a sufficient time with at least one lactone flavor compound.

22. A process according to claim 21 wherein the natural source is selected from an animal source including butter fat, chicken fat, beef tallow, and fish oil.

23. A process according to claim 21 wherein the natural source is selected from a botanical source including cocoa butter, hazelnut oil, peanut oil, and coconut fat.

* * * * *